United States Patent
Huang et al.

[19]

[11] Patent Number: 6,080,149
[45] Date of Patent: Jun. 27, 2000

[54] METHOD AND APPARATUS FOR MONITORING SOLID TISSUE HEATING

[75] Inventors: Alexander L. Huang, Menlo Park; Sharon A. Riddle, Santa Clara; Peter F. Lyons, San Jose, all of Calif.

[73] Assignee: Radiotherapeutics, Corporation, Sunnyvale, Calif.

[21] Appl. No.: 09/005,288

[22] Filed: Jan. 9, 1998

[51] Int. Cl.[7] .................................................. A61B 18/04
[52] U.S. Cl. .............................. 606/32; 606/34; 606/41; 324/600; 346/33 ME; 345/14; 345/38; 345/39
[58] Field of Search ................................. 606/34, 32, 41, 606/38, 42, 45–52; 600/547; 607/98–102, 96, 113; 323/234, 318, 352, 364, 911; 346/33 ME; 324/600; 345/33–40, 44–50, 10, 14

[56] References Cited

U.S. PATENT DOCUMENTS

| | | | |
|---|---|---|---|
| 5,370,675 | 12/1994 | Edwards et al. | 607/101 |
| 5,423,808 | 6/1995 | Edwards et al. | 606/34 |
| 5,437,664 | 8/1995 | Cohen et al. | 606/42 |
| 5,458,597 | 10/1995 | Edwards et al. | 606/41 |
| 5,472,441 | 12/1995 | Edwards et al. | 606/41 |
| 5,486,161 | 1/1996 | Lax et al. | 604/22 |
| 5,496,312 | 3/1996 | Klicek | 604/34 |
| 5,514,129 | 5/1996 | Smith | 606/40 |
| 5,536,267 | 7/1996 | Edwards et al. | 606/41 |
| 5,540,681 | 7/1996 | Strul et al. | 606/42 |
| 5,556,396 | 9/1996 | Cohen et al. | 606/42 |
| 5,562,703 | 10/1996 | Desai | 606/210 |
| 5,599,345 | 2/1997 | Edwards et al. | 606/41 |
| 5,599,346 | 2/1997 | Edwards et al. | 606/41 |
| 5,662,680 | 9/1997 | Desai | 606/210 |
| 5,817,091 | 10/1998 | Nardella et al. | 606/35 |

FOREIGN PATENT DOCUMENTS

| | | |
|---|---|---|
| WO 93/08757 | 5/1993 | WIPO . |
| WO 95/09577 | 4/1995 | WIPO . |
| WO 95/13113 | 5/1995 | WIPO . |
| WO 95/20360 | 8/1995 | WIPO . |
| WO 96/04860 | 2/1996 | WIPO . |
| WO 96/29946 | 10/1996 | WIPO . |
| WO 97/06739 | 2/1997 | WIPO . |
| WO 97/06740 | 2/1997 | WIPO . |
| WO 97/06855 | 2/1997 | WIPO . |
| WO 97/06857 | 2/1997 | WIPO . |

*Primary Examiner*—Linda C. M. Dvorak
*Assistant Examiner*—Bryan K. Yarnell
*Attorney, Agent, or Firm*—Townsend and Townsend and Crew LLP

[57] ABSTRACT

Improved methods and apparatus for monitoring the delivery of radio frequency (RF) energy from electrodes disposed in tissue for inducing hyperthermia and other purposes. In one form, an impedance display of a power supply comprises an array of discrete light elements, where the number of light elements illuminated increases in response to a percentage increase in calculated impedance. The array of light elements is typically arranged in a non-linear pattern where a left hand portion of the array extends horizontally while a right hand portion extends upwardly. The display allows an operator to visually monitor abrupt increases in impedance between an RF instrument and a target tissue. Such increases are used to determine acceptable power ranges to achieve a maximum sustainable delivery of radio frequency energy to the tissue consistent with complete, rapid, and uniform heating of the tissue.

10 Claims, 6 Drawing Sheets

METHOD AND APPARATUS FOR MONITORING SOLID TISSUE HEATING

CROSS-REFERENCE TO RELATED APPLICATIONS

The present invention is related to U.S. patent application Ser. No. 08/936,294, filed on Sep. 25, 1997, now U.S. Pat. No. 5,954,717, and U.S. patent application Ser. No. 08/858,414, filed on May 19, 1997, pending. The full disclosure of these applications are incorporated herein by reference.

BACKGROUND OF THE INVENTION

1. Field of the Invention

The present invention relates generally to the use of radio frequency energy for heating and necrosing solid tissue. More particularly, the present invention relates to a control method and system for delivering radio frequency current to the tissue through an electrode or electrode array disposed within the tissue.

The delivery of radio frequency energy to target regions within solid tissue is known for a variety of purposes. Of particular interest to the present invention, radio frequency energy may be delivered to diseased regions in target tissue for the purpose of tissue heating and/or necrosis, referred to generally as hyperthermia. For example, the liver is a common depository for metastases of many primary cancers, such as cancers of the stomach, bowel, pancreas, kidney and lung. Electrosurgical probes for deploying single and multiple electrodes have been designed for the treatment and necrosis of tumors in the liver and other solid tissues. See, for example, the references cited in the Description of the Background Art hereinafter.

A primary goal in such hyperthermic treatments, particularly those intended for tumor treatment, is the complete, thorough, and uniform heating of the target tissue mass. Uniform heating of the tissue mass, however, can be difficult to achieve, particularly in highly vascularized tissues where variability in local blood flow can have a significant effect on the heating characteristics of the tissue. For example, creation of a lesion having a selected volume in some highly perfused tissue locations may require twice as much power as an identically-sized lesion in less highly perfused locations. While a variety of approaches for achieving such complete, thorough, and uniform heating of tissue have been proposed, most such approaches are somewhat complex and require the use of electrodes which are capable of measuring temperature, or the like. See, for example, the radio frequency power supply described in published PCT Application WO 93/08757. In general, many approaches for achieving uniform tissue heating have relied on slow, gradual heating of the tissue in order to avoid the formation of steam or charred or otherwise necrosed tissue which results in high radio frequency impedance regions within the target tissue mass. Such approaches, however, are complex, can result in an undesirable prolongation of the treatment, and are not always successful.

For these reasons, it would be desirable to provide improved treatment methods, systems, and apparatus which allow for effective and efficient delivery of a radio frequency energy to solid tissue masses using electrodes. In particular, it would be desirable to provide such methods, systems, and apparatus which are useful with many or all tissue-penetrating electrode systems which are now available or which might become available in the future. The methods, systems, and apparatus should be simple to implement and use, and should preferably reduce the complexity, cost, and treatment time required to achieve complete heating and/or necrosis of the target tissue mass. The methods, systems, and apparatus should preferably require no information or feedback from the tissue region being treated, other than information which can be acquired from the power delivery characteristics which can be monitored in the radio frequency power delivery system itself. In particular, the methods, systems, and apparatus should be able to operate solely by monitoring the power and/or current delivery characteristics of the radio frequency energy into an electrode system present in the target tissue. Preferably, monitoring information will be presented in an intuitive manner on a display coupled to or near the power delivery system. At least some of these objective will be met by the present invention as claimed hereinafter.

2. Description of the Background Art

The heating of solid tissue with radio frequency current using the preferred electrode structures of the present invention is described in WO 96/29946 and co-pending applications Ser. Nos. 08/410,344; 08/559,072; 08/766,154; 08/764,085; and 08/858,414, filed on May 19, 1997, the full disclosures of which are incorporated herein by reference.

WO 97/06739; WO 97/06740; WO 97/06855; and WO 97/06857 describe RF treatment electrodes and note that power delivery can "impede out" if levels of power delivered are raised too high.

Assignee of the present application has developed a radio frequency power supply (Model RF-2000, RadioTherapeutics Corporation, Mountain View, Calif.) which provides power levels up to 100 W and is intended for the coagulation (ablation) of soft tissue. The power supply is controlled by a programmable microprocessor which is capable of continuously monitoring power delivered to an electrode system.

Patents and published applications describing radio frequency tissue ablation using electrodes having various configurations include U.S. Pat. Nos. 5,662,680; 5,599,346; 5,599,345; 5,562,703; 5,536,267; 5,486,161; 5,472,441; and 5,458,597; and published International Applications WO 97/06857; WO 97/06855; WO 97/06740; WO 97/06739; WO 96/04860; and WO 95/13113.

A radio frequency power supply having impedance monitoring capability is described in WO 93/08757.

Other radio frequency power apparatus and methods are described in U.S. Pat. Nos. 5,556,396; 5,514,129; 5,496,312; 5,437,664; and 5,370,645; and WO 95/20360, WO 95/09577, and WO 95/20360.

SUMMARY OF THE INVENTION

The present invention provides improved methods and apparatus for monitoring the delivery of radio frequency (RF) energy from electrodes disposed in tissue for inducing hyperthermia and other purposes. It has been found that the delivery of radio frequency power to electrode(s) disposed in tissue can, if the power is delivered for a sufficient time and/or at a sufficient power delivery level or flux, result in an abrupt increase in the electrical impedance between the electrode(s) and tissue. While such an abrupt increase in impedance is undesirable since it results in an immediate fall-off of energy delivery (for a voltage limited radio frequency power source), the present invention relies on the occurrence of the abrupt reduction in power delivery (which may be observed as a reduction in current delivery to the electrodes) to provide information about the heat capacity and heat delivery characteristics of the local target tissue region. Such information is used to control subsequent delivery of energy to the target tissue region using the same electrode(s).

As described in co-pending U.S. patent application Ser. No. 08/936,294, filed on Sep. 25, 1997 (Attorney Docket No. 16807-000900), an abrupt rise in the electrode-tissue interface impedance diminishes very rapidly when the power delivery is stopped, typically disappearing within several seconds. Delivery of the radio frequency power can be resumed after the impedance has diminished, typically to impedance levels substantially equal to those observed prior to the abrupt increase. Based on these observations, it is possible to determine improved or optimized radio frequency power delivery levels and protocols based on the power levels and/or time periods required to induce the abrupt impedance increases and associated power declines in specific target locations. In particular, the protocols rely on appropriate adjustments to the power levels which are resumed after the tissue impedance diminishes.

In a first particular aspect of the present invention, a power supply for use in RF tissue ablation is provided with a unique impedance display which enables the user to concurrently perform the methods described in the copending U.S. patent application Ser. No. 08/936,294, filed on Sep. 25, 1997 (Attorney Docket No. 16807-000900). The power supply comprises a radio frequency power source having a power output, a power return, a voltage signal, and a current signal. The power supply has means for calculating impedance within the target tissue based on the voltage and current signals. To provide feedback to the operator on instrument-tissue interface impedance, the power supply provides an impedance display electronically coupled to the calculating means. The display typically has an image of a bar graph where the bar graph changes in length in response to changes in calculated impedance. The display may be a flat panel display or some other type of display device.

In one embodiment, the impedance display comprises of an array of discrete light elements, where the number of light elements illuminated with respect to a baseline increases in response to an increase in calculated impedance. The baseline will be measured and assigned some number of elements which will be illuminated. The activation and deactivation of light elements is in response to changes, usually percentage changes, relative to the baseline impedance. The array of light elements is typically arranged in a non-linear pattern where a left hand portion of the array extends horizontally while a right hand portion curves upwardly.

In general, the radio frequency energy is supplied as a radio frequency current using a controlled voltage or constant voltage power supply. The use of such radio frequency power sources is preferred because the limited voltage available necessarily results in a reduction of current when the electrode/tissue impedance rises. In addition to allowing the monitoring of impedance based on observing the power or current delivered to the electrodes, the limited voltage also decreases the likelihood of arcing or sparking from the electrode into the tissue. Usually, the power supply will be operated at a level which depends on the size of the electrode, the target tissue type, and the degree of tissue perfusion. Typically, the power supply will provide power in the range from 10 W to 200 W, during all phases of the above-described methods. For prolonged treatment, the electrodes will generally be energized at a power between 20 and 100 W which is in the range from 50% to 90% of the local maximum power level, usually from 70% to 80%.

In a second aspect of the present invention, a method for providing impedance information to an operator comprises the steps of measuring a baseline level of impedance and displaying an image of a length of a bar graph, where the length represents the baseline level of impedance. As the procedure proceeds, the changes in impedance are measured, and the length of the bar graph is changed in response to measured changes in impedance. In one embodiment, the displaying step may comprise illuminating a number of individual light elements of an array of discrete light elements, where the number represents the baseline level of impedance. Changes in impedance are displayed by changing the number of illuminated light elements. For example, a predetermined number of light elements are lit to represent a baseline value of impedance. The number of illuminated light elements are increased if impedance increases by about 2 to 10% and decreased if the number of light elements if impedance decreases by about 5 to 20%. The percentage increases or decreases required to activate or deactivate a light element may be altered as desired to provide the optimal resolution and/or smoothing of impedance changes displayed.

A further understanding of the nature and advantages of the invention may be realized by reference to the remaining portions of the specification and the drawings.

DESCRIPTION OF THE SPECIFIC EMBODIMENTS

I. Overview of Radio Frequency Treatment

Treatments according to the present invention will usually be effected by passing a radio frequency current through the target tissue region in a monopolar or bipolar manner. The specific electrode probes and methods described hereinafter illustrate a monopolar application of radio frequency current to the patient, where a treatment electrode is positioned in the target tissue and a passive or dispersive "electrode" is disposed against the patient's skin to complete a return path for the radio frequency circuit being created. Alternatively, a type of monopolar operation may be employed where the dispersive return electrode is mounted on a portion of the electrode probe being used for treatment. In that case, the area of the dispersive electrode is maximized in order to decrease any heating effect which might occur from current flux at the return electrode. Further alternatively, the methods of the present invention can employ bipolar treatment where paired treatment electrodes are employed to both form the complete circuit and to heat the tissue therebetween.

The desired radio frequency power is preferably supplied at a frequency in the range from 300 kHz to 1.2 MHz, with a conventional sinusoidal or non-sinusoidal wave form. Preferably, a power supply of the present invention described below will operate with a fixed or controlled voltage so that power and current diminish with an increase in observed impedance. Preferred power supplies will operate at relatively low fixed voltages, typically below 150 V (peak-to-peak), usually being from 50 V to 100 V will be preferred. Such radio frequency power supplies are available from RadioTherapeutics Corporation, assignee of the present application, as well as other commercial supplies. In all cases, current will be selected to provide an operating power generally in the range from 10 W to 100 W, usually have a sinusoidal wave form, but optionally having other wave forms.

It will be appreciated that with a fixed or controlled voltage, the power delivered will depend on the current and the impedance present in the circuit. Generally, as described in detail below, methods for RF treatment will begin with delivering power at levels which do not result in excessive electrode/tissue interface impedances until the tissue is fully necrosed. At some point in the treatment protocols of the present invention, power/current may be increased resulting in a more rapid heating of the tissue. In such a case, rapid heating will induce a hard or abrupt increase in the impedance between the tissue electrodes and the adjacent tissue, as previously described. The power supply operates at a constant voltage and in both cases will thus be unable to maintain current levels through the increased tissue impedance. Power is substantially reduced as current drops off since power falls as the square of the decrease in current.

Figure 1:
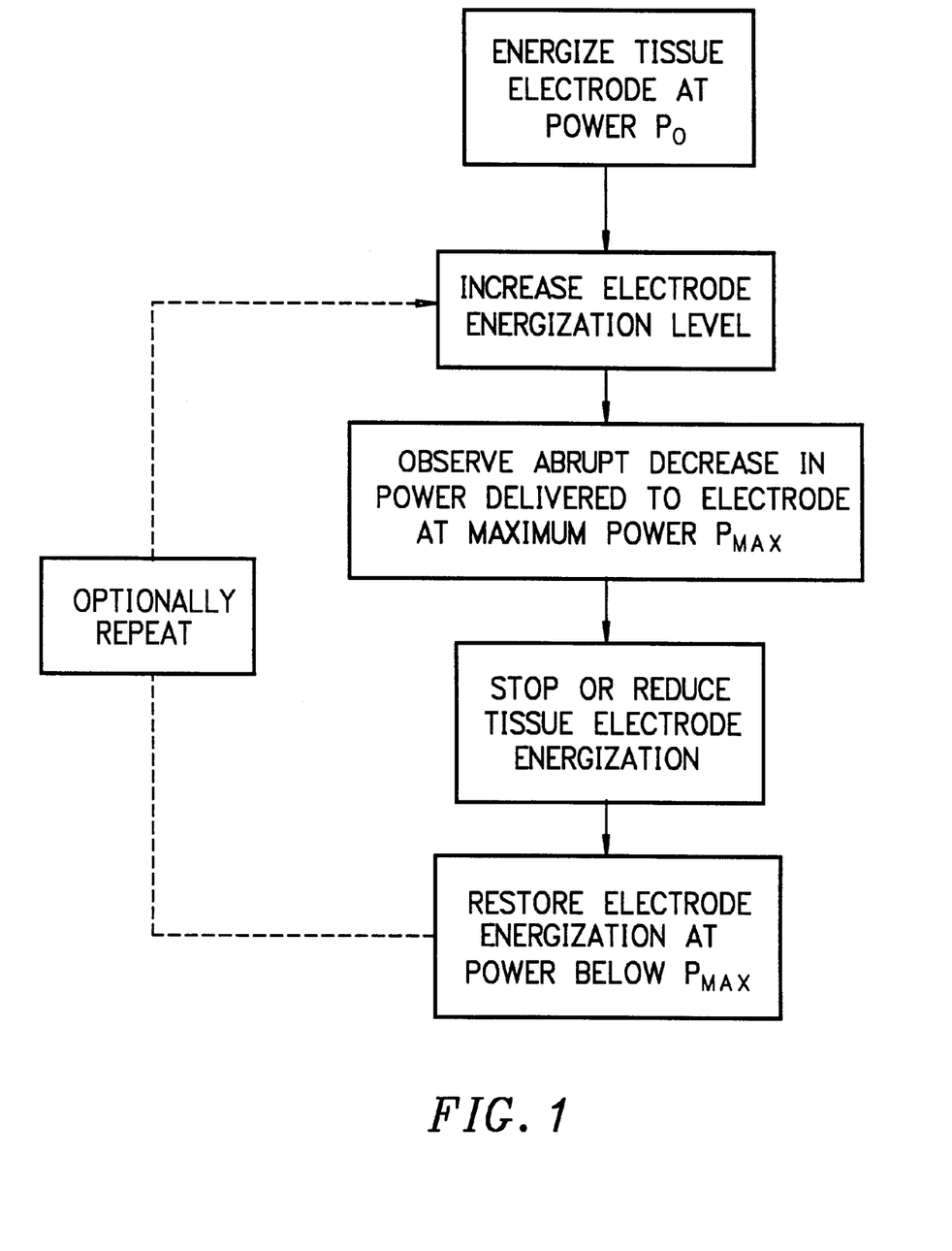
FIG. 1 is a flow chart illustrating the method steps for radio frequency surgery which may be implemented manually or as part of an automatic control system.

Referring now to FIG. 1, methods for RF energy treatment will be generally described. Such methods will rely on energizing tissue electrodes disposed within tissue to heat the tissue for a variety of hyperthermic therapeutic purposes. The electrode(s) will be energized with radio frequency current generally within the power ranges set forth above. Initially, the electrode(s) will be energized at a power $P_0$, with an initial energization lasting long enough to establish a base tissue temperature, which may either be constant or may be gradually increasing, i.e. at a rate less than about 10° C./min., usually less than about 5° C. The electrode energization will then be increased above the initial power level $P_0$, by either a rapid increase or gradual increase protocol as described in more detail below.

In both protocols, the level of power delivered to the tissue will eventually cause an abrupt increase in the impedance between the electrode(s) and the adjacent tissue, which in turn results in observation of an abrupt decrease in the power delivered to the electrode(s). Conveniently, both the decrease in power and the change in impedance is calculable by measuring the current and voltage delivered from the power supply itself. Thus, there is no need to measure impedance, temperature, or any other characteristics directly within the patient tissue or at the electrode/tissue interface. Power at which such decrease occurs is defined herein as the maximum power $P_{MAX}$. The abrupt increase in impedance and decrease in power delivered to the electrode(s) is dependent on a number of factors such as tissue type, the degree of local blood perfusion, and the tissue temperature prior to the power increase. In all cases, at the local value of $P_{MAX}$, the abrupt impedance increase/power decrease will occur over a very short period of time, typically in the range from 10 seconds to 20 seconds. The increase in impedance results from the formation of a thin layer of gas over the electrodes which begins as discrete, isolated bubble(s) at particular sites on the electrode surface. Surprisingly, such local bubble formation quickly spreads over most or all of the electrode surface area so that the power delivered to the electrodes quickly drops to a uniformly low density. Thus, power delivered to the tissue will be reduced, typically by an amount in the range from 70% to 95%, usually in the range from 85% to 95%, based on the initial power level $P_0$.

Determination of the maximum power level is useful in a variety of ways to determine an appropriate treatment power level, as described in more detail below. It is believed that a power limiting impedance typically results from a very thin gaseous layer formed over all or a portion of the electrode surface, and it is further believed that cessation of energization allows the thin gaseous layer to cool very rapidly and to dissipate. Usually, the radio frequency power source will be completely de-energized for a period of time sufficient to permit the bubble layer to dissipate and the tissue impedance to return to its low impedance condition, typically from 3 seconds to 20 seconds, usually from 5 seconds to 10 seconds. It is not necessary, however, to completely shut off power so long as it is reduced sufficiently to allow the temperature and impedance to lower.

After the impedance has returned to its low impedance state, the energization of the electrodes will be restored at a power level selected to maximize delivery of radio frequency energy to the target tissue without prematurely terminating treatment due to the high impedance/low power delivery condition described above. In some cases, however, it will be desirable to optionally repeat the intentional inducement of the high impedance/low power delivery state in order to further optimize power delivery, as discussed in more detail below.

Figure 2:
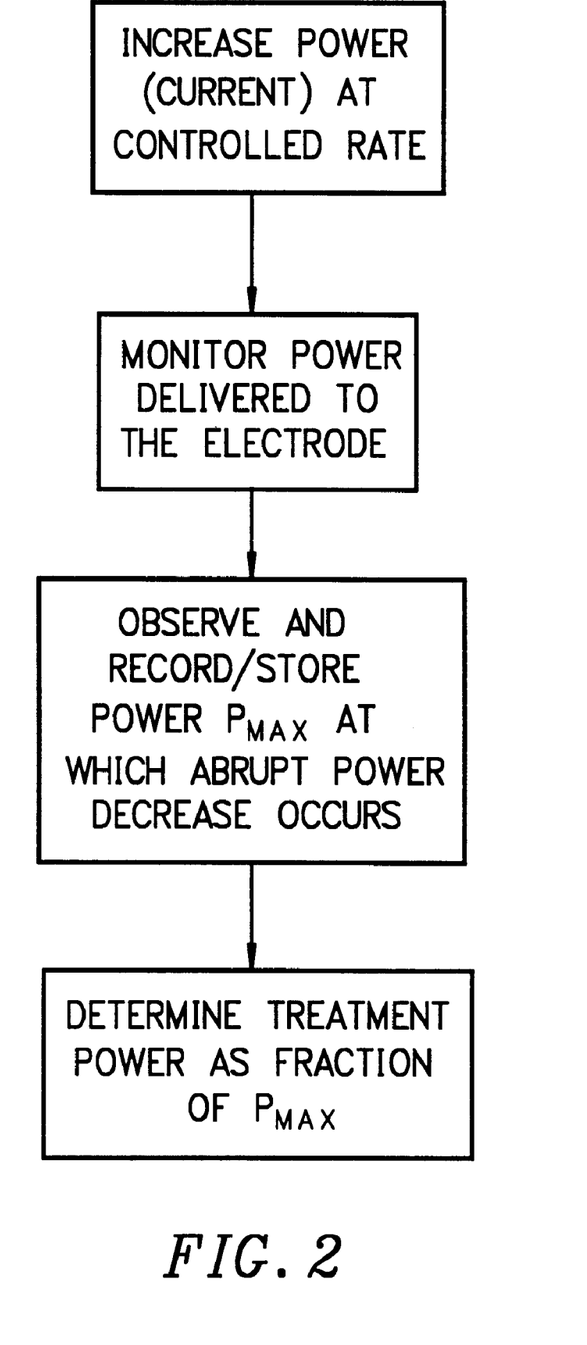
FIG. 2 is a flow chart illustrating an exemplary method for determining a treatment power level which may be implemented as part of the general method illustrated in FIG. 1.

Referring now to FIG. 2, a first preferred protocol for inducing the abrupt impedance increase/power decrease and determining a desired treatment power level is described.

Power being delivered to the tissue electrodes is increased at a controlled rate, typically in the range from 1 W/min. to 25 W/min., preferably from 10 W/min. to 15 W/min. The power is preferably increased linearly at a specific rate within these ranges via a linear increase in voltage until the impedance increases. Actual power delivered to the electrode is monitored, either visually by the operator or automatically by a control system. At some point, which may occur from 2 minutes to 10 minutes after initiating the power increase, usually occurring from 3 minutes to 5 minutes after the initiation of the power increase, the impedance at the electrode-tissue interface will abruptly increase, causing a decrease in the level of power being delivered to the electrodes. The power which was delivered to the electrodes immediately prior to the abrupt decrease is considered to be the maximum power ($P_{MAX}$) deliverable to the electrodes for that particular treatment location. The subsequent treatment power level can thus be determined as a fraction or percentage of the maximum power $P_{MAX}$, typically being from 50% to 90% of $P_{MAX}$, preferably from 70% to 75% of $P_{MAX}$.

The particular protocol illustrated in FIG. 2 is desirable in its simplicity. It can readily be implemented manually, i.e. without the use of an automatic digital controller, by an operator gradually increasing the delivered power rate by manually adjusting the power supply (either continuously or more usually in shortly spaced increments within the ranges set forth above), but is also suitable for automatic implementation. Other suitable protocols for RF surgery are described in U.S. patent application Ser. No. 08/936,294, filed on Sep. 25, 1997 (Attorney Docket No. 16807-000900), the full disclosure of which has been incorporated herein by reference.

Figure 3:
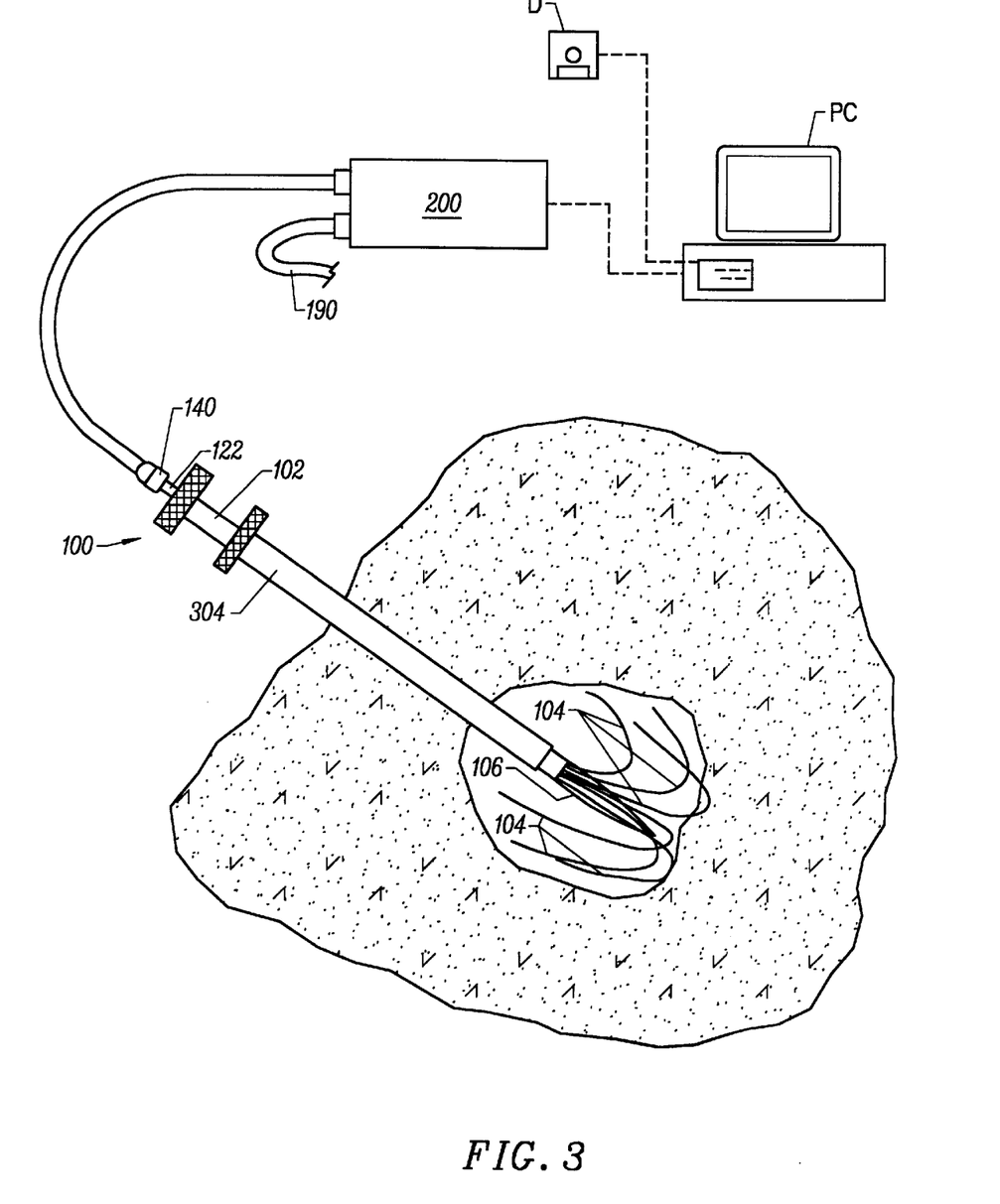
FIG. 3 is a schematic of a system according to the present invention for radio frequency surgery.

Referring now to FIG. 3, a probe system 100 for use in the above described protocol includes a cannula 102 and a plurality of individual electrodes 104 constrained within the cannula over the outer cylindrical surface of a core member 106. The cannula 102 is only partly illustrated with a proximal length broken-off. The entire cannula will typically have a length in the range from about 5 cm to 30 cm, preferably from 10 cm to 20 cm, and outer diameter in the range from 1 mm to 5 mm, preferably from 1.3 mm to 4 mm, and an inner diameter in the range from 0.7 mm to 4 mm, preferably from 1 mm to 3.5 mm. The cannula may be formed from metals, plastics, or the like, and may be electrically active or inactive within the probe system 100, depending on the manner in which electrical energy is to be applied.

Electrodes 104 are connected at their proximal ends to a reciprocatable shaft 122. The core 106 is also secured to the distal end of cylindrical block 120 so that the core and electrodes move together as the shaft 122 is advanced distally or retracted proximally relative to the cannula 102. As the core 106 moves with the electrodes, it will be appreciated that the core will enter the tissue at the same time as the electrodes 104. Thus, the core 106 is shown to have a sharpened distal end 124 to enhance tissue penetration. The core 106 may be electrically coupled to the electrodes 104 (in which case it acts as an additional electrode of the same polarity as electrodes 104) or may be electrically isolated from the electrodes. When the core is electrically isolated, it can remain neutral during a treatment protocol, or alternatively it may be energized in the opposite polarity and thus act as a return electrode in a bipolar treatment protocol.

A connector 140 at the proximal end of shaft 122 may then be connected to an electrosurgical power supply 200. Suitable power supplies are available from commercial suppliers as listed above. A second connecting cable 190 extends from the electrosurgical power supply 200 to a dispersive plate electrode (not shown) on the patient for monopolar operation.

The probe system description presented above is mainly for general illustrative purposes and should not be considered as limiting the scope of the present invention. That is, the invention can be adapted for use with a variety of other RF surgical instruments. Variations of the above described system such as variations in design, location of RF power connections, software operation and structure, specific algorithms used in some software subroutines, configuration of RF probes, and other modifications are possible.

II. Power Supply

Figure 4:
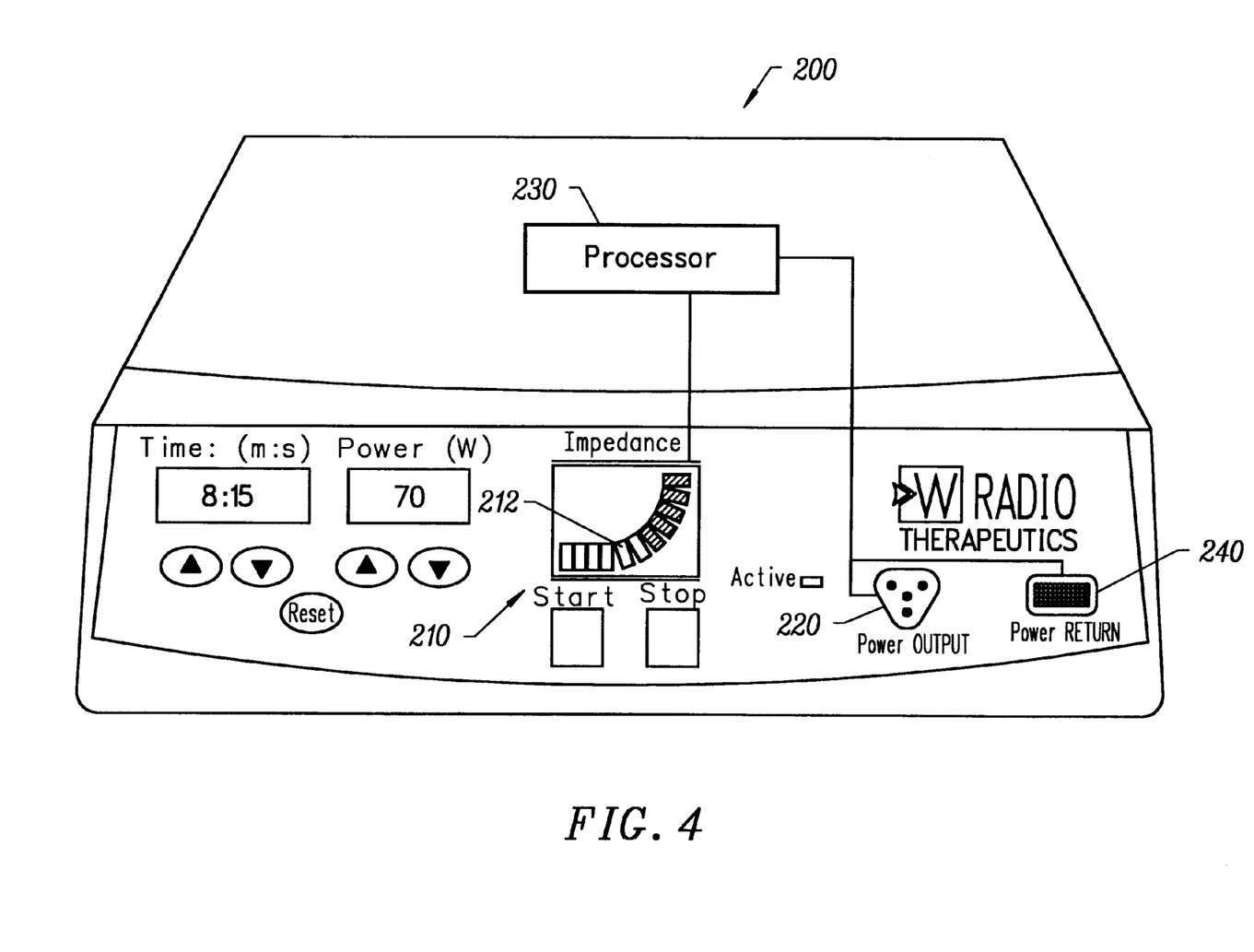
FIG. 4 is a schematic view of a power supply according to the present invention.

Referring to FIG. 4, an electrosurgical power supply 200 of the present invention will preferably have adjustable power outputs, typically by varying the voltage to set current and power, and will permit monitoring of the actual power and calculated electrode/tissue impedance delivered to the electrodes being used to treat the patient. The power supply 200 can deliver at least 80 watts to the probe system 100, more preferably at least 90 watts, and most preferably at least 100 watts. The methods may be performed manually, i.e. by an operator manually adjusting the power levels and observing the electrode/tissue impedance and power deliveries on a conventional power supply.

Optionally, but not necessarily, the power supply may be used with a digital controller which may be incorporated within the electrosurgical power supply 200, situated between the electrosurgical power supply and the patient, or which may be interfaced with a properly equipped power supply. The use of a computer interfaced with a power supply is illustrated in FIG. 3. The power supply 200 will also usually include a monitoring/control interface. The computer PC may employ any operating system compatible with the electrosurgical power supply 200, the computer will typically be interfaced using a conventional cable. The methods of the present invention may be delivered to the personal computer PC and thus to the electrosurgical power supply 200 by programming the computer in any conventional manner. A floppy disk D or other computer memory component may be used in order to implement the program within the computer. Any other manner of delivering computer readable code and instructions into the computer may also be utilized, including compact disk, tape, read only memory (ROM), and delivery of instructions via a modem and/or over the internet. An exemplary power supply having the power and computer interface capabilities suitable for the present invention is the Model RF-2000 (shown in FIG. 4), available from RadioTherapeutics Corporation, Mountain View, Calif., assignee of the present application.

III. Power Supply Display

Figure 5:
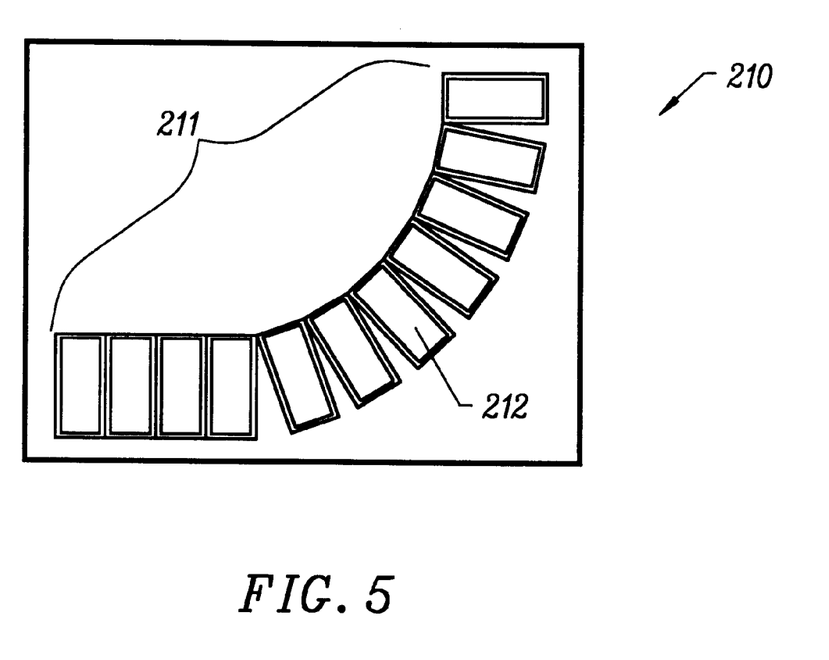
FIG. 5 shows an exemplary embodiment of an impedance display according to the present invention.

Referring now to FIGS. 4 and 5, an impedance display 210 for use with an electrosurgical power supply 200 will now be described. A power supply 200 having an impedance display 210 allows an operator to visually monitor impedance changes encountered by the probe system 100. The impedance display 210 on the power supply includes an image of a bar graph 211 which increases or decreases in length in response to changes in calculated impedance. The display may use flat panel displays such as a liquid crystal display (LCD) or other types of devices such as cathode ray tube monitors to show the operator the real time level of impedance. The operator may use this information to adjust the level of power delivery from the supply 200 as desired.

In a preferred embodiment, the display 210 comprises of an array of discrete light elements 212, such as an array of light emitting diodes (LEDs), arranged in a nonlinear pattern. Although not limited in this manner, the nonlinear pattern of the array of discrete light elements 212 preferably defines a line or a segmented bar graph where the left hand portion of the array is horizontal and the right hand portion curves upwardly. In a specific preferred embodiment, four light elements 212 comprise the horizontal portion while seven light elements 212 comprise the upwardly curved portion. The curved right hand portion created by the light elements 212 mimics the shape of an x-y plot of impedance versus time. This upwardly curving shape accentuates the change in level much more than if the bar simply extended in a straight line. This makes the interpretation of the display 210 more intuitive to the operator. Such a display is also more visible and easily understood by the physician or other operator who will typically be standing five to ten feet away from the power supply during use. It should also be understood that the display 210 does not need to be directly connected to the power supply 200 and may be a separate standalone unit.

In the exemplary embodiment, the power supply 200 obtains impedance information by sensing output RF voltage signal and output RF current signal from a power outlet 220. A processor 230 calculates the impedance based on the voltage and current signals from the power outlet 220 and a power return 240. The impedance encountered by the probe system 100 may be derived by dividing the voltage by the current. Impedance measurements are made across a patient-isolation boundary using medically-isolated voltage and current sensors known in the art. This presently measured impedance is then compared, typically by processor 230, to an initial or baseline impedance value to calculate whether the bar graph 211 should be lengthened or shortened to reflect changes in measured impedance. In a preferred embodiment, the lengthening and shortening of the bar graph 211 involves the illumination or deillumination of individual light elements 212.

As described above, during typical radio frequency surgical procedures, a small amount of power is applied to the probe system 100 to measure an initial or baseline impedance in the system. The small amount of power, typically 1 watt or more, is supplied to the system 100, and the baseline impedance calculated. The calculated impedance is then treated as the baseline for all subsequent impedance determinations. The baseline is initially displayed as a predetermined length of the bar graph 211. In embodiments using discrete light elements 212, a predetermined number of discrete light elements 212 (typically four horizontal elements) on the display 210 are illuminated to represent the baseline impedance (regardless of the actual value of the baseline). This establishes an initial point of visual reference for the operator during the procedure. Changes in the impedance calculated by the system 100 within the target tissue causes changes in the length of the bar graph 211 or the number of illuminated light elements 212.

Preferably, the percentage change in impedance required to increase or decrease the length of the bar graph 211, or the number of illuminated light elements 212, is graduated to keep the rate of change of the bar graph fairly smooth as the RF treatment proceeds. For example in one embodiment of the power supply 200, when the four horizontal elements 212 are illuminated, it takes about a 5 to 20%, preferably 10% or more, drop in impedance for at least one of the illuminated light elements to go out. However, an increase of about 2 to 10%, preferably 5% or more, illuminates at least the next discrete light element 212. The number of light elements 212 responding to changes in impedance may also be varied. Although not limited in this manner, it may be necessary in some scenarios for multiple light elements 212 to be illuminated or deilluminated with each change in impedance. As observed in FIG. 6, the changes in the impedance shown by line 250 are nonlinear and may require this graduated illumination or scaling to provide proper resolution to display the impedance changes occurring during the procedure. It should be understood that the percentage change in impedance required to light or unlight each element 212 or change the length of the bar graph 211 may be customized to provide the desired level of resolution for various radio frequency surgical procedures.

Figure 6:
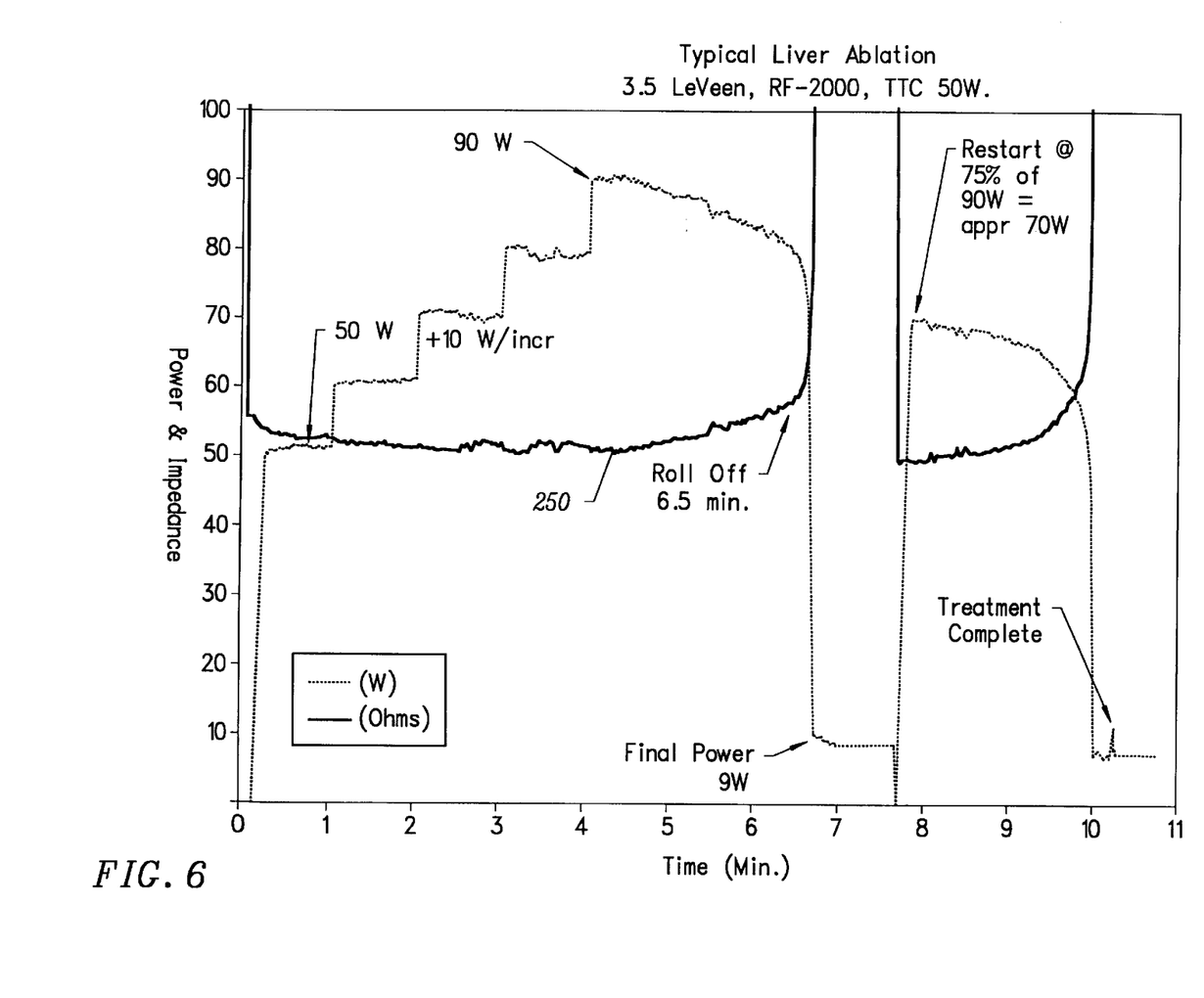
FIG. 6 is a graph of power and impedance levels encountered during an radio frequency surgical procedure.

The operator may use the impedance information displayed on the display 210 to either decide when to shut off or reduce power to the probe system 100 as described in FIG. 1. The power level and impedance levels for a typical liver ablation procedure is shown in FIG. 6. Alternatively, in situations where the power supplied to the system 100 is automatically controlled, the display 210 is used for monitoring and observational purposes.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A power supply comprising:
a radio frequency power source having a power output, a power return, a voltage signal, and a current signal;
means for calculating impedance based on the voltage and current signals; and
an impedance display electronically coupled to said means for calculating impedance, said display having an image of a bar graph wherein said graph changes in length in response to changes in calculated impedance;
wherein the image of the bar graph comprises light elements arranged in a nonlinear pattern, wherein a left hand portion of the array is horizontal and the right hand portion curves upwardly and the number of light elements illuminated increases in response to an increase in calculated impedance.

2. A power supply comprising:
a radio frequency power source having a power output, a power return, a voltage signal, and a current signal;
means for calculating impedance based on the voltage and current signals;
an impedance display electronically coupled to said means for calculating impedance, said display having an image of a bar graph wherein said graph changes in length in response to changes in calculated impedance; and
means for determining a baseline impedance and subsequent changes in impedance relative to the baseline, wherein the display changes the bar graph length based on the relative changes in impedance to reflect a change between a baseline impedance and a presently measured impedance.

3. A power supply as in claim 2 wherein the bar graph comprises discrete light elements and the supply further comprises means for determining the number of discrete light elements to illuminate to reflect the change between a baseline impedance and a presently measured impedance.

4. A method for providing impedance information to a operator of a radio frequency power supply comprising the steps of:
measuring a baseline level of impedance;
displaying an image of a length of a bar graph, wherein the length represents said baseline level of impedance;
measuring changes in impedance;
comparing presently measured impedance values with the baseline level of impedance to calculate the length of the bar graph to be displayed; and
changing the length of the bar graph to display the calculated length.

5. A method as in claim 4 wherein:
said baseline measuring step comprises measuring an initial impedance by applying a small amount of energy to a power output;
measuring voltages across the power output and a power return; and
dividing voltage by current to derive impedance.

6. A method as in claim 4 wherein:
the displaying step comprises illuminating a number of individual light elements of an array of discrete light elements, wherein the number represents said baseline level of impedance;
said changing step comprises changing the number of illuminated light elements in response to measured changes in impedance.

7. A method as in claim 6 further comprising:
lighting a predetermined number of light elements to represent a baseline value of impedance;
illuminating at least one additional light element in response to an impedance increase of about 2 to 10% of the baseline impedance; and
deilluminating at least one additional light element in response to an impedance decrease of about 5 to 20% of the baseline impedance.

8. A method for radio frequency surgery, said method comprising:
measuring tissue impedance to obtain a baseline impedance;
setting a predetermined length of a bar graph on a real time impedance display of the power supply to the baseline impedance;
delivering radio frequency power to an electrode in tissue from a power supply;
observing changes in electrode/tissue impedance relative to a baseline on a real time impedance display of the power supply; and
decreasing power from the power supply when the impedance observed on the display exceeds a predetermined level.

9. An improved radio frequency power supply of the type having a radio frequency output and an impedance display, wherein the improvement comprises:
 a bar graph having a predetermined length displaying a baseline impedance, wherein the graph is a relative display to the baseline impedance and changes in length in response to changes in measured impedance.

10. An improved power supply of claim 9 wherein:
 the bar graph comprises a curved bar graph of discrete light elements;
 wherein a number of light elements are illuminated in response to a baseline impedance and which the number of illuminated light elements changes in response to changes in measured impedance.

* * * * *